US00PP36638P3

(12) United States Plant Patent
Hansen

(10) Patent No.: US PP36,638 P3
(45) Date of Patent: Apr. 29, 2025

(54) ***CAMPANULA* PLANT NAMED 'Starbright'**

(50) Latin Name: *Campanula carpatica*
Varietal Denomination: Starbright

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 15 days.

(21) Appl. No.: 18/445,830

(22) Filed: Feb. 23, 2024

(65) Prior Publication Data

US 2024/0292772 P1 Aug. 29, 2024

Related U.S. Application Data

(60) Provisional application No. 63/576,688, filed on Feb. 27, 2023.

(51) Int. Cl.
*A01H 5/02* (2018.01)
*A01H 6/26* (2018.01)

(52) U.S. Cl.
USPC ..... Plt./414
CPC ..... *A01H 6/264* (2018.05)

(58) Field of Classification Search
USPC ..... Plt./414
CPC . A01H 5/02; A01H 5/00; A01H 6/264; A01H 6/26
See application file for complete search history.

(56) References Cited

PUBLICATIONS

Proven Winners Rapido White Carpathian Bellflower retrieved on Jun. 16, 2024 at https://www.provenwinners.com/plants/campanula/rapido-white-carpathian-bellflower-campanula-carpatica, 4 pp. (Year: 2024).*

* cited by examiner

*Primary Examiner* — June Hwu

(57) ABSTRACT

A new and distinct bellflower plant, *Campanula* plant named 'Starbright' with a dense, compact, mounded habit; cordate to deltoid medium-green foliage and numerous white campanulate flowers flowering over at least a 14-week period beginning in late spring and continuing until hard frost. The new plant is suitable for landscaping as a specimen, en masse, or in containers.

1 Drawing Sheet

Botanical designation: *Campanula carpatica.*
Cultivar denomination: 'Starbright'.

STATEMENT REGARDING PRIOR DISCLOSURES UNDER 37 CFR 1.77(B)(6)

The claimed plant was first briefly described with a photograph on Dec. 1, 2023, on a website operated by Walters Gardens, Inc. Walters Gardens, Inc. obtained the new plant and all information about the new plant from the inventor. The new plant was first sold in Poland on Feb. 27, 2022, by Danziger who obtained the new plant and all information relating thereto, indirectly from the inventor. No plants of *Campanula* 'Starbright' have been sold in this country or anywhere in the world nor has any disclosure of the new plant been made more than one year prior to the filing date of the provisional application.

BACKGROUND OF THE PLANT

The present invention relates to the new and distinct Bellflower herein also referred to as *Campanula* 'Starbright', by the cultivar name, 'Starbright', or as the new plant. The new plant was derived from a cross made on Jul. 8, 2016, from a plant in a greenhouse research facility in Zeeland, Michigan. The female parent was the proprietary, unreleased, and unnamed selection known only as 15-6-5 (not patented) and the male parent was 'Violet Teacups' U.S. Plant Pat. No. 32,844. The single selected seedling from this cross represented by 'Starbright' was selected from a group of seedlings by the inventor, isolated, compared in subsequent years to other *Campanula* and subsequently found to be different from all cultivars known to the discoverer, and eventually given the breeder code 16-2-2 prior to being assigned a cultivar epithet.

Asexual propagation at the same nursery in Zeeland, MI, USA by basal cuttings has shown 'Starbright' to be stable and reproduce true to type in successive generations since late June 2017.

SUMMARY OF THE PLANT

*Campanula* 'Starbright' has not been observed in all possible environmental conditions. The phenotype may vary slightly with changes in environments such as light intensity, fertility, water availability, etc. without, however any variation in genotype.

*Campanula* 'Starbright' is distinct from all cultivars known to the inventor in the following traits:

1. Small, cordate to deltoid, serrate, medium-green foliage with compact height and dense mounded habit.
2. Flowers are bell-shaped, white, and clustered at the nodes and ends of heavily branched stems.

3. Long flowering period beginning for about 14 weeks beginning late spring and continuing until hard frost.

Plants of *Campanula* 'Starbright' are most similar to plants of the varieties 'Rapido White' (not patented) and 'White Clips' (not patented).

'Rapido White' has a shorter flowering season, less flower coverage in peak flower, the flowers are larger. 'White Clips' has a larger habit and slightly larger flowers with a shorter flowering season.

The female parent has a smaller flower with a purplish-blue color with a slightly lighter center. The male parent has purplish-blue solid-colored flowers.

BRIEF DESCRIPTION OF THE DRAWINGS

The color drawings illustrate the overall characteristics of *Campanula* 'Starbright' as a five-year-old plant. The colors are as true as reasonably possible given the technology available. The color values may vary slightly depending on light intensity and quality.

DETAILED BOTANICAL DESCRIPTION

Figure 1:
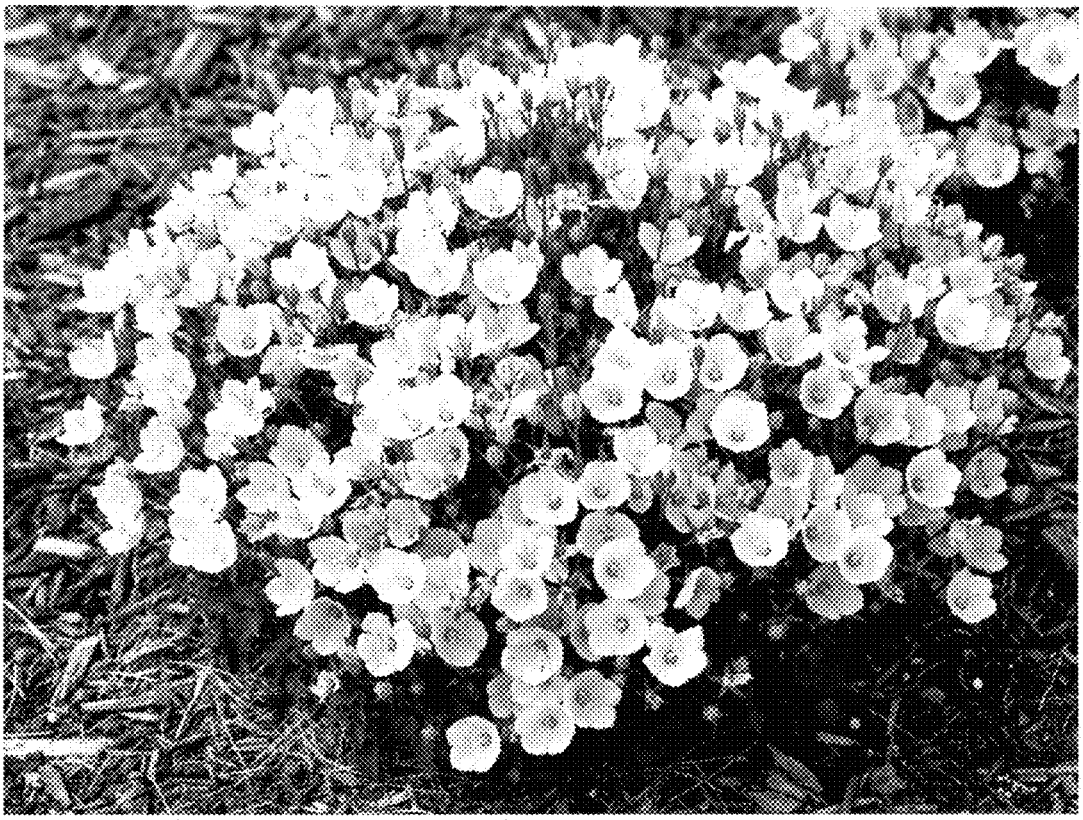
FIG. 1 shows the new plant in a landscape environment.
Figure 2:
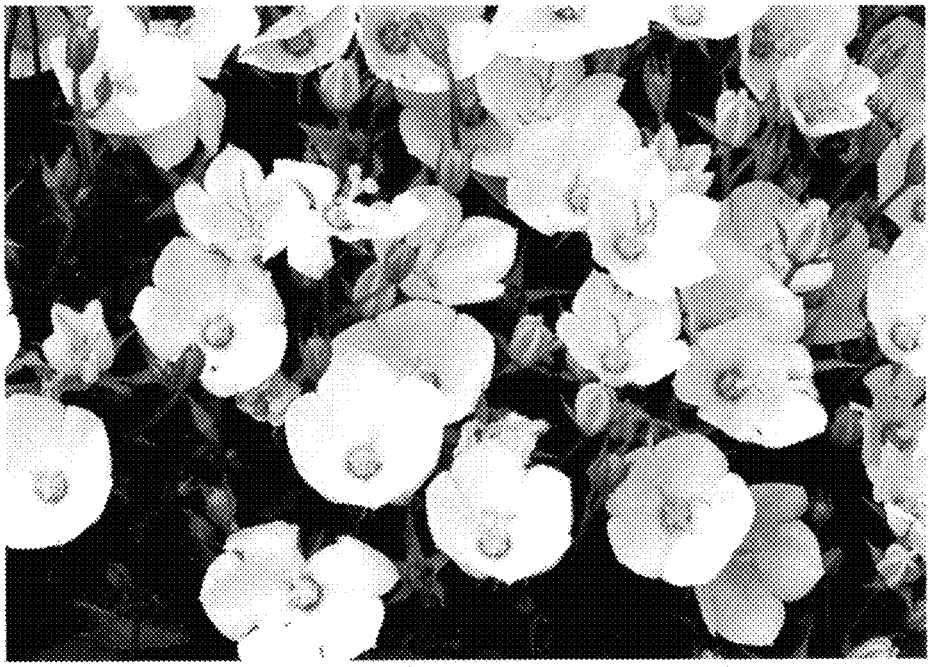
FIG. 2 shows a close-up of the flowers and buds of the new plant.

The following description is based on one and five-year-old plants growing in a full-sun trial garden and a partially shaded greenhouse in Zeeland, MI, USA. Except for ordinary dictionary color usage, color references are according to The Royal Horticultural Society Colour Chart, sixth edition, 2015. The new plant has not been observed in all possible growing conditions and may vary in phenotypic characteristics based on water availability, light conditions, fertilizer, temperatures, etc. without varying in genotypic characteristics.

Parentage: Female or seed parent is 15-6-5; the male parent is 'Violet Teacups';

Asexual propagation: Cuttings, about 12 to 20 days to initiate roots; time to finish in a one-gallon container about 12 weeks from an established 25 mm plug;

Plant habit: Rounded mound, herbaceous, perennial, winter-hardy; with heavily-branched flower stems up to 42 cm wide and 28 cm tall in flower; with about 20 well-branched stems per plant;

Roots: Finely branched; color nearest RHS NN155B;

Stems: Flexible; glabrous; thin; cylindrical with slight longitudinal ridges; to about 24 cm long and 3 mm diameter at base;

Stem color: Young stems nearest RHS 138B; mature stems nearest RHS 146D toward base, and nearest RHS 146B distally, no anthocyanins observed;

Leaves: Alternate; simple; cordate to deltoid; acute apex; truncate to cordate base; margin irregularly serrate shallowly to less than 1 mm; adaxial and abaxial surfaces glabrous, matte; to about 38 mm long and 28 mm wide; margin undulation weak;

Leaf color: Young expanding leaves adaxial nearest RHS 146A and abaxial nearest RHS 146C; mature leaves adaxial between RHS 137B and RHS N137C, abaxial between RHS 137C and RHS 137D;

Petiole: Thin; concavo-convex; glabrous both adaxial and abaxial; margin entire and sparsely hispidulous; to about 55 mm long and 2.5 mm wide at base;

Petiole color: Emerging leaves nearest RHS 146D adaxial and abaxial, mature leaves adaxial and abaxial nearest RHS 138B;

Veins: Palmate; glabrous adaxial; puberulent, glabrate abaxial;

Vein color: Adaxial midrib nearest RHS 145C and RHS 148D and secondary veins, abaxial midrib nearest RHS 148C and secondary veins between RHS 146A and RHS 147B;

Flower: Single; perfect; complete; campanulate; on terminal branches; to about 24 mm across, about 18 mm long; aspect upright to outwardly; typically, one to five flowers per branch;

Inflorescence fragrance: Not detected;

Calyx: Broadly campanulate; horizontal; to about 16 mm wide and extending about 4 mm above corolla base;

Sepals: Typically, five; lanceolate; narrowly acute apex; truncate base; margin serrulate; glabrous adaxial and abaxial; about 10 mm long and about 2 mm wide at base;

Sepal color: Abaxial and adaxial nearest RHS 138A;

Flowering period: For about 14 weeks beginning late spring and continuing until hard frost; producing about 150 flowers and 100 buds per plant at one time during peak flowering;

Flower longevity: Individually about 5 to 7 days;

Flower buds: One day prior to opening—oblong; longitudinally channeled; rounded apex; about 14 mm long and 8 mm diameter;

Flower bud color: One day prior to opening—nearest RHS 155A;

Peduncle: About 30 per plant; highly branched; cylindrical to ridged; glabrous; aspect upright to outwardly; flexible; about 3 mm diameter at base and 22 cm long; about 15 nodes, average internode spacing about 2 cm; branches to about 7.5 cm long and 2 mm diameter at base;

Peduncle color: Nearest 138B;

Pedicel: Cylindrical to striate; glabrous; thin, flexible; average about 18 mm long and 0.5 mm diameter;

Pedicel color: Nearest RHS 138B;

Petals: Typically five, rarely six or seven; ovate; acute apex; basal 8 mm fused; corolla tube to about 8 mm long and about 6 mm across below fusion; glabrous adaxial and abaxial; without spots on adaxial or abaxial;,margin entire; about 15 mm long and 10 mm wide above fusion; without petaloid lobes;

Petal color: Adaxial nearest RHS NN155D in maturity with veins in the proximal one-third nearest RHS 148D; abaxial nearest RHS NN155D;

Androecium: Typically, five;

*Filament.*—Distally cylindrical, proximally applanate and adpressed along ovary; glabrous; about 5 mm long and 1.5 mm wide at base and 0.1 mm thick; color nearest RHS 145C.

*Anther.*—Lanceolate; basifixed; about 3 mm long and 1.5 mm across; color nearest RHS 159B.

*Pollen.*—Not abundant; color between RHS 162C and RHS 162D.

Gynoecium: Syncarpous; half-inferior; about 14 mm long;

*Style.*—Cylindrical; arcuate to reflexed; puberulent distally, glabrous distally; about 8 mm long and 0.5 mm diameter; color nearest RHS NN155B.

*Stigma.*—Typically, trifid, rarely quad-fid or penta-fid; cochleate distally with maturity; about 6 mm long before curling, 3 mm long when curled, and 0.5 mm diameter; color nearest RHS 145C.

Fruit: Oblong poricidal capsule; longitudinally carinate; 8 mm tall and 4.5 mm wide;

Fruit color: Nearest RHS N200A;

Seed: Flattened ellipsoidal; rounded apex and base; about 1 mm long and 0.5 mm across center;

Seed color: Variable, some seeds between RHS 200A and RHS N200A; *Campanula* 'Starbright' is tolerant of winter temperatures from USDA hardiness at least to zones 3 to 8. The new plant grows best in full-sun with good drainage and adequate moisture. It is not known to be tolerant of diseases and pests that are common to other *Campanula* cultivars.

I claim:

1. A new and distinct cultivar of *Campanula* plant named 'Starbright' as herein described and illustrated.

* * * * *